United States Patent

Benda et al.

[11] Patent Number: 6,071,863
[45] Date of Patent: Jun. 6, 2000

[54] BIODEGRADABLE POLYALPHAOLEFIN FLUIDS AND FORMULATIONS CONTAINING THE FLUIDS

[75] Inventors: Rainer Benda, Brussels, Belgium; John V. Bullen, Berkshire, United Kingdom; Alan J. Plomer, Rixensart, Belgium

[73] Assignee: BP Amoco Corporation, Chicago, Ill.

[21] Appl. No.: 08/860,758

[22] PCT Filed: Nov. 13, 1996

[86] PCT No.: PCT/US96/18169

§ 371 Date: Aug. 11, 1997

§ 102(e) Date: Aug. 11, 1997

[87] PCT Pub. No.: WO97/18280

PCT Pub. Date: May 22, 1997

[30] Foreign Application Priority Data

Nov. 14, 1995 [GB] United Kingdom ............... 9523246

[51] Int. Cl.⁷ .................. C10M 107/02; C10M 169/04
[52] U.S. Cl. ................... 508/591; 585/7; 585/10; 585/12; 585/18
[58] Field of Search ............................ 508/591

[56] References Cited

U.S. PATENT DOCUMENTS

| 4,218,330 | 8/1980 | Shubkin | 252/46.6 |
| 5,284,989 | 2/1994 | Apelian et al. | 585/533 |
| 5,595,966 | 1/1997 | Rees et al. | 508/591 |

FOREIGN PATENT DOCUMENTS

| 468109 A1 | 1/1992 | European Pat. Off. |
| 558835 A1 | 9/1993 | European Pat. Off. |
| 613873 A2 | 9/1994 | European Pat. Off. |
| WO 97/18280 | 5/1997 | WIPO |

OTHER PUBLICATIONS

International Search Report, PCT/US96/18169, Amoco Corporation et al., Apr. 1997.

*Primary Examiner*—Ellen M. McAvoy
*Attorney, Agent, or Firm*—James R. Henes; Stephen L. Hensley

[57] ABSTRACT

Biodegradable polyalphaolefin fluids which are useful in functional fluid and lubricant compositions are oligomers of mixtures of $C_{12}$ and $C_{14}$ alphaolefins. The fluids have kinematic viscosities at 100° C. of from 5 to 20 mm²/s and a biodegradability as determined by the CEC L-33 A93 test of at least about 50 percent.

12 Claims, No Drawings

BIODEGRADABLE POLYALPHAOLEFIN FLUIDS AND FORMULATIONS CONTAINING THE FLUIDS

This invention relates generally to synthetic fluids prepared by oligomerizing linear α-olefins and more particularly to a synthetic fluid having improved biodegradability which is an oligomer of a mixture of $C_{12}$ and $C_{14}$ alpha-olefins.

Alpha-olefin oligomers, commonly referred to as polyalphaolefins or PAOs, and their use as hydraulic fluids and lubricants (synlubes) are well known. The oligomers are usually prepared from 1-decene for optimum properties, although mixtures of α-olefins have been used, as described, for example, in U.S. Pat. Nos 3,330,883 and 3,576,898. One advantage of the α-olefin fluids is that they are more biodegradable than mineral oil basestocks of like viscosity. This property is important from an environmental standpoint, especially in applications such as hydraulic fluids for earth- and water-moving equipment, automotive crankcase oils, heavy duty diesel oils, 2-stroke oils, automatic transmission fluids, and automotive gear oils. Biodegradability, however, tends to decrease as the viscosity of the fluids increases (higher oligomers). Surprisingly, we have found that oligomers made from certain $C_{12}$ and $C_{14}$ α-olefin mixtures have enhanced biodegradability compared to 1-decene based fluids.

In accordance with this invention there is provided a polyalphaolefin fluid which comprises an oligomer prepared from a mixture of $C_{12}$ and $C_{14}$ olefins, said mixture having a linear, terminal mono-olefin content of at least about 80 weight percent and a $C_{12}$ olefin content of from about 40 to about 90 weight percent, said fluid having a kinematic viscosity of from about 5.0 to about 20 $mm^2/s$ at 100° C. and a biodegradability as determined by the CEC L-33 A93 test, of at least about 50 percent.

Also provided is a functional fluid or lubricant composition, said composition comprising a polyalphaolefin fluid which comprises: (a) an oligomer prepared from a mixture of $C_{12}$ and $C_{14}$ olefins, said mixture having a linear, terminal mono-olefin content of at least about 80 weight percent and a $C_{12}$ olefin content of from 40 to 90 weight percent, said fluid having a kinematic viscosity of from 5.0 to 20 $mm^2/s$ at 100° C. and a biodegradability, as determined by the CEC L-33 A93 test, of at least about 50 percent, and (b) at least one additive selected from the group consisting of dispersants, antioxidants, anti-wear agents, antifoamers, corrosion inhibitors, detergents, seal-swell agents and viscosity improvers.

$C_{12}$ and $C_{14}$ α-olefin mixtures for forming the oligomer can be prepared by mixing substantially pure 1-dodecene and 1-tetradecene. Conveniently, commercially available mixtures such as those obtained from the Ziegler chain growth process, which usually contain up to about 20 weight percent of vinylidene and internal olefins, can also be used. The mixtures may also contain up to about 5 weight percent of $C_{10}$ and/or $C_{16+}$ olefins. Because the use of higher carbon number olefins raises the pour point of the oligomers compared to 1-decene oligomers, the proportion of $C_{14}$ olefin should be kept at or below about 60 weight percent, such that the mixtures contain from 40 to 90 weight percent $C_{12}$ olefin, preferably from about 55 to about 80 weight percent $C_{12}$ olefin and, more preferably, from 60 to 75 weight percent $C_{12}$ olefin, with the remainder being $C_{14}$ olefin and up to about 5 weight percent of higher or lower carbon number olefins.

The oligomers can be prepared as known in the art, preferably using a Friedel-Crafts catalyst system. The preferred Friedel-Crafts catalyst is $BF_3$. Pure $BF_3$ is not an effective oligomerization catalyst and the use of a small amount of a polar compound is necessary.

Any of the known promoters for $BF_3$ can be used such as water, alcohol (e.g. methanol, ethanol, n-propanol, isopropanol, n-butanol, isobutanol, n-hexanol, 2-ethyl hexanol, n-decanol, and n-dodecanol including mixtures thereof), fatty acids (e.g. valeric and caproinic), organic esters (e.g. butyl acetate, methyl valerate and ethyl octanoate), ketones (e.g. methyl ethyl ketone and methyl isobutyl ketone), ethers (e.g. dibutyl ether, tetrahydrofuran and dioxane), alkoxylated alcohols (e.g. 2-ethoxy-ethanol), polyhydric alcohols (e.g. glycol and glycerol), inorganic acids (e.g. phosphoric acid), silica and zeolites.

The preferred promoters are water and alcohols containing about 1–8 carbon atoms such as methanol, ethanol, isopropanol, n-propanol, n-butanol, isobutanol, n-hexanol and n-octanol. The more preferred promoters are alcohols containing about 2–5 carbon atoms. The most preferred promoter is n-butanol.

The amount of promoter should be an amount that causes the $BF_3$ to act as an oligomerization catalyst. This is referred to as a promoter amount. A suitable range is 0.01–2.0 weight percent of the α-olefin, and, preferably, 0.1 to 1.0 percent.

Methods of conducting a $BF_3$ catalyzed oligomerization process are well known. In one mode, $BF_3$ is merely bubbled through a promoter-containing α-olefin reaction mixture during the oligomerization. In a preferred mode, the process is conducted under $BF_3$ pressure. A useful pressure is from 15 to 1000 kPa, preferably from 40 to 500 kPa and more preferably from 75 to 150 kPa.

The preferred reaction temperatures are 10 to 60° C. and more preferably 25 to 50° C. Lower temperatures will increase the amount of higher oligomers but at the cost of a slower reaction rate. High temperatures give a fast reaction rate but increased yield of dimer.

The oligomerization is usually conducted until the monomer content of the reaction mixture drops below about 5 weight percent, more preferably below about 2 weight percent. The reaction product, which is predominantly (above 50 weight percent) trimer and higher oligomers and, preferably, 30 to 80 weight percent trimer is washed to remove the $BF_3$ and promoter and the monomer is stripped. If desired the product can be distilled to obtain different viscosity cuts. The product fluids can by hydrogenated by conventional methods in order to improve their stability. Supported nickel catalysts are useful. For example, nickel on a Kieselguhr support gives good results. Batch or continuous processes can be used. For example, the catalyst can be added to the liquid and stirred under hydrogen pressure or the liquid may be trickled through a fixed bed of the supported catalyst under hydrogen pressures of 700 to 7,000 kPa at temperatures of at 150 to 300° C.

Fluids of the invention which have a 100° C. kinematic viscosity of at least about 5 $mm^2/s$, and especially from 5.5 to 7.5 $mm^2/s$, are, surprisingly significantly more biodegradable than 1-decene fluids of the same viscosity range.

The fluids of the invention are useful in various functional fluid and lubricant applications and their properties can be enhanced by the use of conventional lubricant additives in total amounts of up to about 25 weight percent, and preferably from 0.1 to 20 weight percent. Such additives include, for example, dispersants, anti-oxidants, anti-wear agents, anti-foam, corrosion inhibitors,. detergents, seal swell agents and viscosity index improvers. These types of additives are well known in the art. Some examples of such additives are zinc dialkyl-dithiophosphates, calcium aryl sulfonates, overbased calcium aryl sulfonates, barium phenates, barium oxide-neutralized reaction products of phosphorus pentasulfide and terpenes of high molecular weight olefins, hindered alkyl phenols, methylene-bis-dialkyl phenols, dibutyl tin sulfide, dibutyl hydrogen phosphonate, tri-cresyl-phosphate, high molecular weight alkyl succinimides of ethylene-polyamines such as tetraethylene-polyamine, sulfur-bridged alkyl phenols, sulfurized fatty acid esters and amides, silicones and dialkylesters. Proprietary combinations of such additives, "additive packages," which are tailored for specific base oils and applications, are commercially available from several sources including Ethyl Corporation. Viscosity Index (VI) improvers are separately available.

The over-all biodegradability of the formulations containing the fluids of the invention will depend upon the total functional fluid or lubricant blends including the lubricant additives.

The fluid can be used as base oils or additive oils and in blends with other oils such as, for example, $C_6$–$C_{10}$ 1-olefin based PAO's, mineral oils, synthetic esters.

Lubricant formulations of the fluids have been found to have a higher viscosity index and to exhibit a much lower tendency than 1-decene oligomer to form deposits in Panel Coker Tests.

Surprisingly, it has also been found that when heavy duty diesel engine lubricants are formulated using the fluids of the invention, a significant reduction in particular exhaust emissions occurs when compared with both mineral oil and conventional 1-decene oligomer based lubricants. For significant particulate reduction the base oil should contain at least about 50 weight percent $C_{12}/C_{14}$ PAO and, preferably, at least about 85 weight percent.

The invention is further illustrated by, but is not intended to be limited to, the following Examples.

EXAMPLE 1

$C_{12}/C_{14}$ olefin which contains about 70% $C_{12}$ and 30% $C_{14}$ by weight, with about 85 mole % being linear α-olefin, is oligomerized using a $BF_3$-n-butanol catalyst at a reaction temperature of about 30° C. (2.7 barg $BF_3$ pressure, 0.6 weight % of the monomer charge of n-butanol) for about 85 minutes cook time. The oligomer yield is about 95%. The crude product is washed, filtered and distilled to remove monomer and some dimer. The product is then hydrogenated. The product contains, by weight, about 15% dimer, 54% trimer and 31% tetramer and higher oligomers.

EXAMPLE 2

Example 1 is repeated except that the reaction temperature is about 45° C. and the cook time is about 75 minutes. The crude product is distilled to remove all of the monomer and dimer, and then is hydrogenated. The product contains, by weight, about 68% trimer and 32% tetramer and higher oligomers.

The rheological properties of fluids prepared in Examples 1 and 2 were compared with those of a commercial 6 mm$^2$/s polyalphaolefin fluid marketed by Albemarle Corporation under the trademark, DURASYN™ 166.

| TEST | Ex. 1 $C_{12}/C_{14}$ PAO | DURASYN ™ 166 PAO | Ex. 2 $C_{12}/C_{14}$ PAO |
|---|---|---|---|
| K. Visc 100° C., mm$^2$/s | 6.16 | 5.90 | 7.09 |
| K. Visc 40° C., mm$^2$/s | 31.91 | 31.00 | 39.57 |
| Viscosity Index | 145 | 137 | 142 |
| Pour Point, ° C. | −39 | −69 | −39 |
| C.C.S. −30° C., mPa · s | 2233 | 2343 | 3200 |
| Flash Point, ° C. (PMC) | 226 | 227 | 260 |
| NOVACK, % wt loss | 7.90 | 7.00 | 4.50 |

The biodegradability of the 6 mm$^2$/s product of Example 1 was compared to that of the DURASYN™ 166 PAO under the conditions of the CEC L33 A93 test.

The CEC (Coordinating European Council) L33 A93 protocol was developed to determine the persistence of 2-stroke outboard engine oil in aquatic environments. In recent years, results from this test have been applied more broadly. The test is fast becoming a standard for aquatic biodegradability for water insoluble materials. It should be noted that this test is not a test of "ready biodegradability" but "comparative biodegradability." These terms are tightly defined by regulatory bodies.

The CEC L 33 A93 test procedure is summarized as follows: Test flasks, together with poisoned flasks, (each in triplicate) containing mineral medium, test oil and inoculum are incubated for 0 to 21 days. Flasks containing calibration materials in the place of the test oil are run in parallel. At the end of the incubation times, the contents of the flasks are subjected to sonic vibration, acidified, and extracted with $CCl_4$ or R113. The extracts are then analyzed by Quantitative IR Spectroscopy, measuring the maximum absorption of the $CH_3$-band at 2930 cm$^{-1}$. The biodegradability is expressed as the % difference in residual oil content between the test flasks and the respective poisoned flasks at day 21.

The results are shown in Table I.

TABLE I

Percentage Biodegradability (CEC L-33 A93)

| | EMPA[1] | Ref Oil[2] | BfB[3] | Ref Oil[4] |
|---|---|---|---|---|
| $C_{12}/C_{14}$ PAO | 70.00 | 87.00 | 69.70 | 92.70 |
| DURASYN ™ 166 PAO | 40.00 | 87.00 | 28.00 | 94.70 |

[1]EMPA = Swiss Federal Laboratory for Material Testing
[2]Ref. Oil was RL 130
[3]BfB = BFB Consultants
[4]Ref Oil was RL 130

The 6 mm$^2$/s PAO was also compared with the 6 mm$^2$/s 1-decene based PAO in Panel Coker Bench Tests both as pure PAO and in SAE 5W40 heavy duty diesel oils (HDDO) formulations. The $C_{12}/C_{14}$ fluids, in each case, exhibited a much lower tendency to produce deposits. The results are shown in Tables II and III.

TABLE II

Panel Coker Performance - Pure PAOs

Test Conditions

Panel Temperature: 320° C.
Test Length: 18 hrs.
Splash Pattern: 15s splash 45s bake

TABLE II-continued

Panel Coker Performance - Pure PAOs

Sump Oil Temperature: 140° C.
Air Flow: 6.30 ltr hr$^{-1}$

Weight of Deposit, mg

|  | Test No. 1 | Test No. 2 | Test No. 3 | Test No. 4 | Average |
|---|---|---|---|---|---|
| DURASYN ™ 166 PAO | 509.0 | 510.0 | 528.0 | 655.0 | 551.0 |
| $C_{12}/C_{14}$ PAO | 120.0 | 95.00 | 155.0 | 157.0 | 132.0 |

TABLE III

Panel Coker Performance - SAE 5W40 HDDOs

Test Conditions

Panel Temperature: 360° C.
Test Length: 18 hrs.
Splash Pattern: 15s splash 45s bake
Sump Oil Temperature: 140° C.
Air Flow: 6.30 ltr hr$^{-1}$ Weight of Deposit, mg

|  | Test No. 1 | Test No. 2 |
|---|---|---|
| SAE 5W40 (DURASYN ™ 166) PAO | 166.0 | 274.0 |
| SAE 5W40 ($C_{12}/C_{14}$) PAO | 50.0 | 80.0 |

EXAMPLE 3

A 5W40 heavy duty diesel oil (HDDO) was formulated using the $C_{12}/C_{14}$ PAO of Example 1 and compared to a reference 15W40 mineral oil based HDDO and a 5W40 HDDO formulated using a 6cSt 1-decene based oligomer fluid (Albemarle DURASYN™ 166) for total particulate emissions. The comparison was done using a modern European heavy duty, direct injection, 6 cylinder in line 5.96 liter diesel engine turbocharged with a charge-air cooler (max power 177 kW at 2600 rpm, max torque 840 Nm) which meets Euro II European Commission Legislation emission standards (Oct. 1995). The comparison was, done using the standard U.S. transient test procedure which simulates a combination of freeway and non-freeway driving with programmed acceleration, deceleration, load and no-load conditions. The formulated oil compositions are shown in Table IV. Two tests were done with each oil and the results are reported in Table V.

TABLE IV

TEST OIL COMPOSITIONS
(By Percentage Weight)

| COMPONENTS | TEST OIL 1 15W40 | TEST OIL 2 5W40 | TEST OIL 3 5W40 |
|---|---|---|---|
| Mineral Base Oil | 78.50 | — | — |
| $C_{12}/C_{14}$PAO | — | — | 55.42 |
| Durasyn ™ 166 PAO | — | 55.42 | — |
| Durasyn ™ 164 PAO | — | 6.78 | 6.78 |
| DI Package | 20.30 | 20.30 | 20.30 |
| VI Improver[1] | 0.90 | 7.50 | 7.50 |
| PPD[2] | 0.30 | — | — |
| Ester[3] | — | 10.00 | 10.00 |
| TOTAL | 100.00 | 100.00 | 100.00 |

NOTES:
[1]A non-dispersant type VI improver which was used in all three test oils which is an hydrogenated polyisoprene polymer.
Test Oil 1: Neat VI polymer was used.
Test Oils 2 and 3: A 15% m/m solution of VI polymer in 6cSt Polyalphaolefin was used.
[2]PPD is pour point depressant.
[3]In test oils 2 and 3 the same ester was used - a POLYOL ester.

TABLE V

Particulate Levels HDDO

| Oil Cold/Warm | 1 | | 2 | | 3 | |
|---|---|---|---|---|---|---|
| Engine Start | C | W | C | W | C | W |
| Particulates[2] Test A | 0.192 | 0.176 | 0.186 | 0.166 | 0.181 | 0.156 |
| Particulates Test B | — | 0.176 | 0.191 | 0.170 | 0.183 | 0.160 |

[1]grams/horsepower/hour collected on the filter.
The results, in duplicate, show a significant reduction in particulates for the $C_{12}/C_{14}$ PAO based lubricant.

What is claimed is:

1. A polyalphaolefin fluid which comprises an oligomer prepared from a mixture of $C_{12}$ and $C_{14}$ olefins, said mixture having a linear, terminal, mono-olefin content of at least about 80 weight percent and a $C_{12}$ olefin content of from about 40 to about 90 weight percent, with the remainder being $C_{14}$ olefins and with only up to about 60 weight percent of $C_{14}$ olefins and only up to about 5 weight percent of olefins having carbon numbers higher than $C_{14}$ or lower than $C_{12}$, said fluid having a kinematic viscosity of from about 5.0 to about 20 mm$^2$/s at 100° C. and a biodegradability, as determined by the CEC L-33 A93 test, of at least about 50 percent.

2. The fluid of claim 1 wherein said mixture of $C_{12}$ and $C_{14}$ olefins has a $C_{12}$ olefin content of from about 55 to about 80 weight percent.

3. The fluid of claim 1 wherein said mixture of $C_{12}$ and $C_{14}$ olefins has a $C_{12}$ olefin content of from 60 to 75 weight percent.

4. The fluid of claim 1 wherein said fluid has a kinematic viscosity of from 5.5 to 7.5 mm$^2$/s at 100° C.

5. The fluid of claim 1 wherein said fluid has a kinematic viscosity of about 6.0 mm$^2$/s at 100° C.

6. A functional fluid or lubricant composition, said composition comprising a polyalphaolefin fluid which comprises: (a) an oligomer prepared from a mixture of $C_{12}$ and $C_{14}$ olefins, said mixture having a linear, terminal, mono-olefin content of at least about 80 weight percent and a $C_{12}$ olefin content of from about 40 to about 90 weight percent, with the remainder being $C_{14}$ olefins and with only up to about 60 weight percent of $C_{14}$ olefins and only up to about 5 weight percent of olefins having carbon numbers higher than $C_{14}$ or lower than $C_{12}$, said fluid having a kinematic viscosity of from about 5.0 to about 20 mm$^2$/s at 100° C. and a biodegradability, as determined by the CEC L-33 A93 test, of at least about 50 percent, and (b) one or more of a dispersant anti-oxidant, anti-wear agent, anti-foam agent, corrosion inhibitor, detergent, seal-swell agent or viscosity improver.

7. The composition of claim 6 wherein the additive content is from 0.1 to 25 weight percent.

8. The composition of claim 6 wherein said mixture of $C_{12}$ and $C_{14}$ olefins has a $C_{12}$ olefin content of from about 55 to about 80 weight percent.

9. The composition of claim 6 wherein said mixture of $C_{12}$ and $C_{14}$ olefins has a $C_{12}$ olefin content of from 60 to 75 weight percent.

10. The composition of claim 6 wherein said fluid has a kinematic viscosity of from 5.5 to 7.5 mm$^2$/s at 100° C.

11. A diesel engine lubricant which provides reduced particulate emissions comprising (a) a base oil which comprises at least 50 weight percent of an oligomer prepared from a mixture of $C_{12}$ and $C_{14}$ olefins, said mixture having a linear, terminal, mono-olefin content of at least about 80 weight percent and a $C_{12}$ olefin content of from about 40 to about 90 weight percent, with the remainder being $C_{14}$ olefins and with only up to about 60 weight percent of $C_{14}$ olefins and only up to about 5 weight percent of olefins having carbon numbers higher than $C_{14}$ or lower than $C_{12}$, said fluid having a kinematic viscosity of from about 5.0 to about 20 mm$^2$/s at 100° C, and (b) one or more of a dispersant, anti-oxidant, anti-wear agent, anti-foam agent, corrosion inhibitor, detergent, seal-swell agent or viscosity improver.

12. The composition of claim 11 wherein the additive content is from 0.1 to 25 weight percent.

* * * * *